(12) United States Patent
Zhao et al.

(10) Patent No.: US 10,674,723 B2
(45) Date of Patent: Jun. 9, 2020

(54) 1,8-BIS(SCHIFF BASE)-P-MENTHANE DERIVATIVES AS WELL AS PREPARATION METHOD AND APPLICATIONS THEREOF

(71) Applicant: INSTITUTE OF CHEMICAL INDUSTRY OF FOREST PRODUCTS, CAF, Nanjing (CN)

(72) Inventors: Zhendong Zhao, Nanjing (CN); Shichao Xu, Nanjing (CN); Shouji Zhu, Nanjing (CN); Jing Wang, Nanjing (CN); Liangwu Bi, Nanjing (CN); Yuxiang Chen, Nanjing (CN); Yanju Lu, Nanjing (CN); Yan Gu, Nanjing (CN)

(73) Assignee: INSTITUTE OF CHEMICAL INDUSTRY OF FOREST PRODUCTS, CAF, Nanjing (CN)

( * ) Notice: Subject to any disclaimer, the term of this patent is extended or adjusted under 35 U.S.C. 154(b) by 33 days.

(21) Appl. No.: 15/793,995

(22) Filed: Oct. 26, 2017

(65) Prior Publication Data

US 2018/0110219 A1    Apr. 26, 2018

(30) Foreign Application Priority Data

Oct. 26, 2016 (CN) .......................... 2016 1 0942979

(51) Int. Cl.
| | |
|---|---|
| *A01N 33/04* | (2006.01) |
| *C07C 251/24* | (2006.01) |
| *A01N 35/10* | (2006.01) |
| *C07C 251/14* | (2006.01) |
| *C07C 249/02* | (2006.01) |
| *C07C 319/20* | (2006.01) |
| *G01R 33/46* | (2006.01) |

(52) U.S. Cl.
CPC ............. *A01N 33/04* (2013.01); *A01N 35/10* (2013.01); *C07C 251/14* (2013.01); *C07C 251/24* (2013.01); *C07C 249/02* (2013.01); *C07C 319/20* (2013.01); *C07C 2601/14* (2017.05); *G01R 33/46* (2013.01)

(58) Field of Classification Search
CPC ...... A01N 33/04; A01N 35/10; C07C 251/24; C07C 251/14; C07C 2601/14; C07C 249/02; C07C 319/20; G01R 33/46
See application file for complete search history.

(56) References Cited

FOREIGN PATENT DOCUMENTS

CN    100486956    5/2009

OTHER PUBLICATIONS

Shi et al., "Synthesis and antimicrobial activities of Schiff bases derived from 5-chloro-salicylaldehyde," European Journal of Medicinal Chemistry, Nov. 2006, pp. 558-564.
CAS Registry on STN, RN856187-45-6, Jul. 2005.

*Primary Examiner* — John Pak
*Assistant Examiner* — Andriae M Holt
(74) *Attorney, Agent, or Firm* — JCIPRNET

(57) ABSTRACT

This invention discloses a type of 1,8-bis(Schiff base)-p-menthane derivatives as well as their preparation method and applications. The reaction of 1,8-diamino-p-menthane with a substituted benzaldehyde was carried out in a polar organic solvent at 0° C.-75° C. for 1-48 h. After the completion of the reaction, part of the solvent was distilled off to perform recrystallization to get a 1,8-bis(Schiff base)-p-menthane derivative, whose pre-emergence herbicidal activity against ryegrass was determined by using the Petri dish seed germination method. The 1,8-bis(Schiff base)-p-menthane derivatives, obtained with this method in high yield and mild reaction conditions, have a good inhibitory effect on the growth of annual ryegrass, and low toxicity.

8 Claims, 11 Drawing Sheets

1,8-BIS(SCHIFF BASE)-P-MENTHANE DERIVATIVES AS WELL AS PREPARATION METHOD AND APPLICATIONS THEREOF

CROSS-REFERENCE TO RELATED APPLICATION

This application claims the priority benefit of China application serial no. 201610942979.3, filed on Oct. 26, 2016. The entirety of the above-mentioned patent application is hereby incorporated by reference herein and made a part of this specification.

BACKGROUND

1. Technical Field

This invention relates to 1,8-bis(Schiff base)-p-menthane derivatives as well as the preparation method and applications thereof. Specifically, it relates to a preparation method of 1,8-bis(Schiff base)-p-menthane derivatives by using 1,8-diamino-p-menthane and substituted benzaldehydes as raw materials to react in a polar organic solvent, as well as the herbicidal application of related products to annual ryegrass.

2. Description of Related Art

Weeds are one of the most important factors affecting agricultural production. They compete with crops for nutrients, moisture, sunlight and space. Some of them are even the intermediate host of pests, thus promoting the occurrence of pests and diseases, and reducing crop yield and quality. Since the middle of the 20th century, synthetic pesticides have become one of the most important weeding methods in agricultural production and have played a pivotal role in increasing global food production. However, synthetic pesticides are highly toxic and are difficult to be biodegraded. Excessive application of pesticides has caused increasingly serious harm to the environment, seriously affecting the food and ecological safety. The development and application of new environmentally friendly pesticides are attracting increasing attention.

Botanical herbicides are pesticides developed from plant resources. Due to their low toxicity, biodegradability and other characteristics, botanical herbicides have become the most widely studied new-type pesticides in recent years. P-menthane (1) monoterpenoids are the most widely distributed terpenoids in nature. Due to their good environmental compatibility and biological activity, p-menthane derived pesticides are being deeply researched and developed and show good development prospects.

Among them, cinmethylin (2), an oxygenated heterocyclic derivative of p-menthane, has already been commercially available. It can effectively inhibit the growth of plant meristems. It has a wide application period, low usage and other advantages (Agrochemicals, 1996 (3): 34-34.).

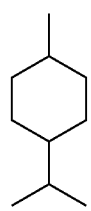

1

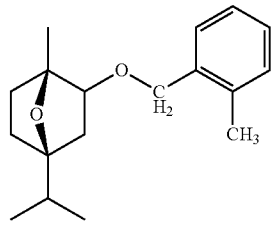

2

Schiff base mainly refers to a class of compounds containing imine or methylenimine group (—RC=N—). Due to their special structural properties, Schiff base compounds have herbicidal, antibacterial, antiviral, anti-tumor and other biological activities. In recent years, the application of Schiff base compounds as pesticides has been increasing. Tang et al. synthesized a series of triazole Schiff base compounds. Studies showed that related compounds have good herbicidal activity against barnyard grass and rape (Chemical Reagents, 2014, 36 (7).). The study conducted by Aggarwal et al. (J. Agric. Food Chem., 2009, 57, 8520-8525) showed that phenyl Schiff base derivatives have good inhibitory effects on *Sclerotium rolfsii* Saccardo and *Rhizoctonia*.

SUMMARY

In order to develop new Schiff base botanical herbicides having a menthane structure to avoid the high toxicity and difficult biodegradation of synthetic pesticides, a type of 1,8-bis(Schiff base)-p-menthane derivative as well as their preparation method and applications are disclosed. The method prepares a type of 1,8-bis(Schiff base)-p-menthane derivatives by using 1,8-diamino-p-menthane to react with substituted benzaldehydes and measures their pre-emergence herbicidal activity against ryegrass by using the Petri dish seed germination method.

The 1,8-bis(Schiff base)-p-menthane derivatives have the following structure:

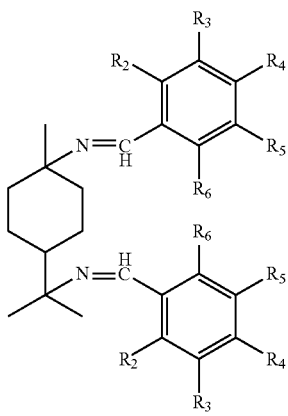

I

In the general formula I, $R_1$~$R_6$ are one or more of hydrogen, an alkyl group, a halogenated alkyl group, a nitro group, a halogen group, or any combinations thereof.

The above-mentioned preparation method of a 1,8-bis (Schiff base)-p-menthane derivative was prepared by reacting 1,8-diamino-p-menthane with a substituted benzaldehyde in a polar organic solvent. After the completion of the reaction, the solvent was distilled to perform recrystallization and get a 1,8-bis(Schiff base)-p-menthane derivative.

The above-mentioned polar organic solvent is any one of methanol, ethanol, tetrahydrofuran, dimethylformamide and dimethylsulfoxide.

The substituted groups of the above-mentioned substituted benzaldehyde are an alkyl group, a halogenated alkyl group, a nitro group, a halogen group, or any combinations thereof.

The reaction temperature is 0° C.~75° C.

The reaction time is 1~48 h.

The above-mentioned 1,8-bis(Schiff base)-p-menthane derivatives are used as a herbicidal active ingredient.

The above-mentioned 1,8-bis(Schiff base)-p-menthane derivatives are used as a herbicide active ingredient against ryegrass.

Beneficial Effects

1. The invention provides a class of new compounds, 1,8-bis(Schiff base)-p-menthane derivatives, as well as their synthesis method and their use in herbicidal activity.

2. The invention provides a simple synthesis process with small environmental pollution and high safety, and can easily achieve industrial scale production.

3. The 1,8-bis(Schiff base)-p-menthane derivatives disclosed in the invention have excellent herbicidal activity. $LD_{50}$ of the root growth of annual ryegrass is less than 1.06 mmol/L, and $LD_{50}$ of the stem growth of annual ryegrass is less than 2.83 mmol/L.

DESCRIPTION OF THE EMBODIMENTS

Analytical Method

Figure 1:
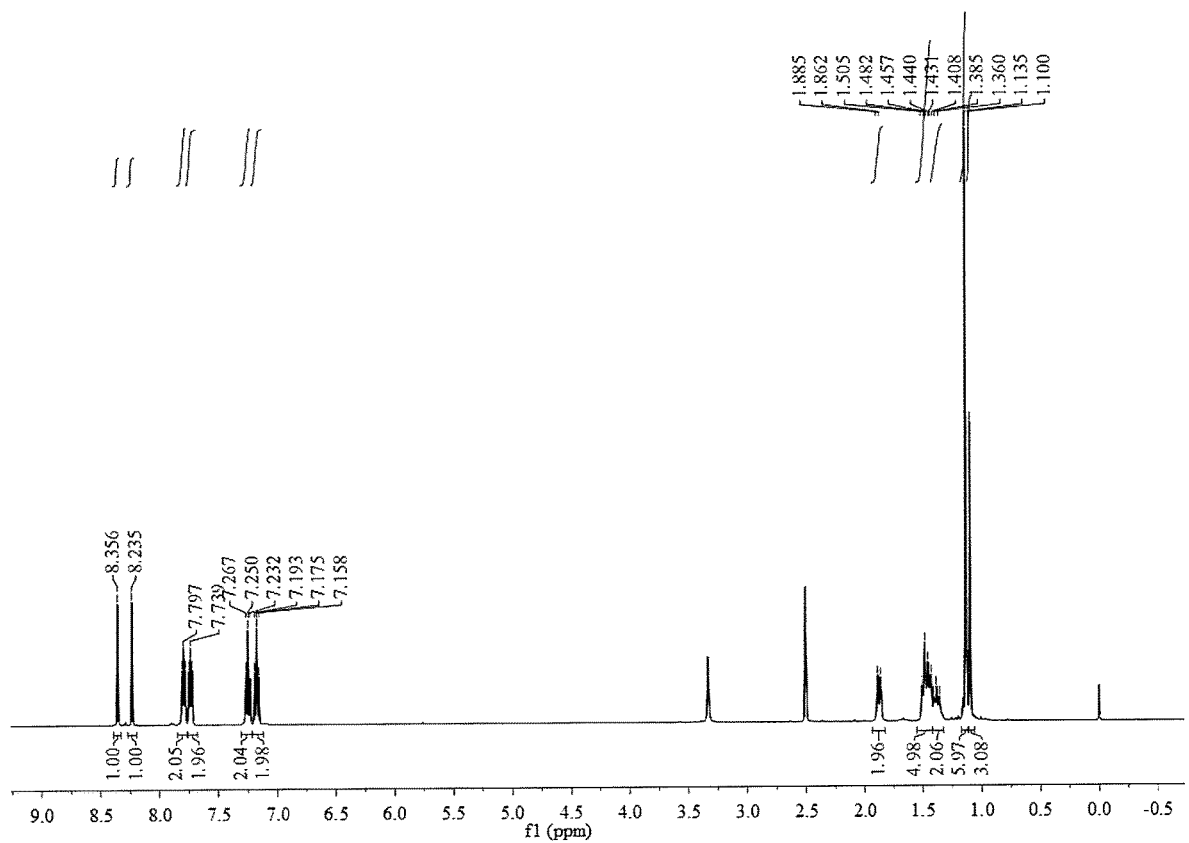
FIG. 1 is a $^1H$ NMR graph of 1,8-bis(2-hydroxyphenylimine)-p-menthane.
Figure 2:
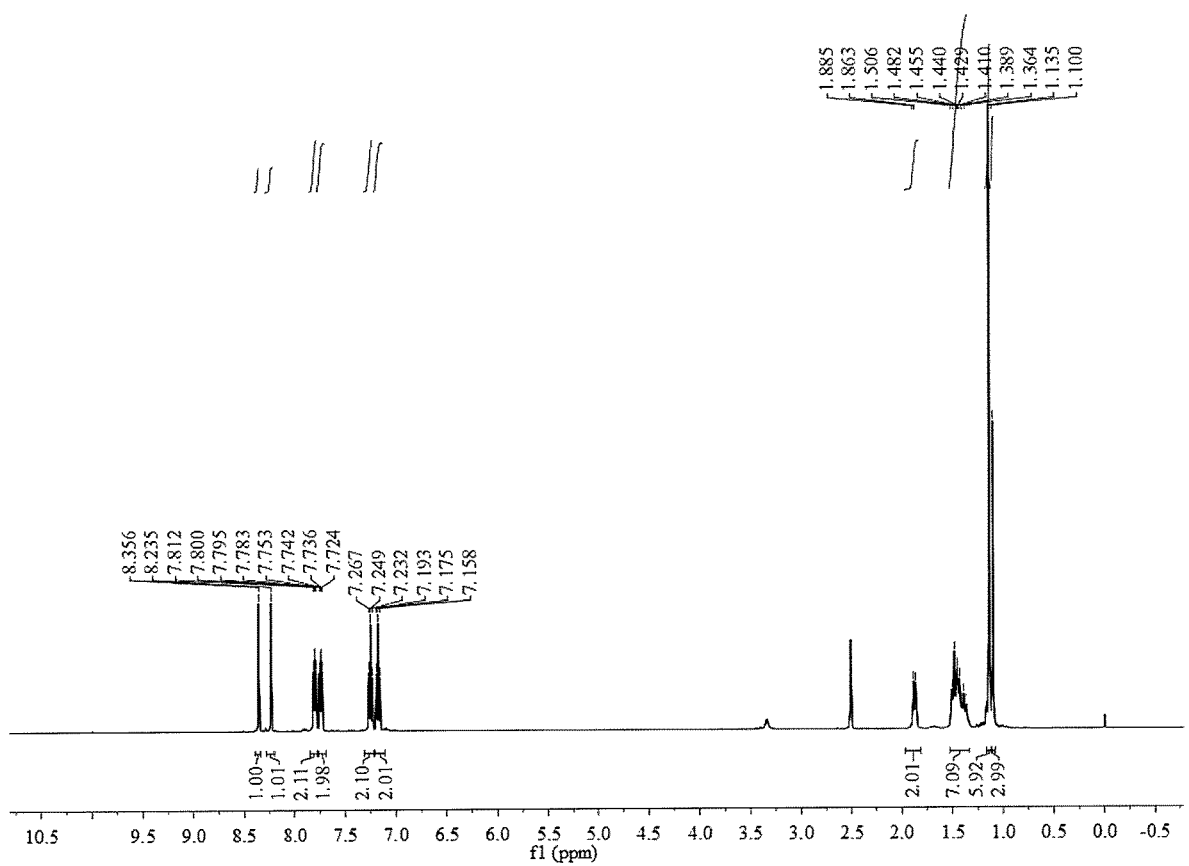
FIG. 2 is a $^1H$ NMR graph of 1,8-bis(4-fluorophenylimine)-p-menthane.
Figure 3:
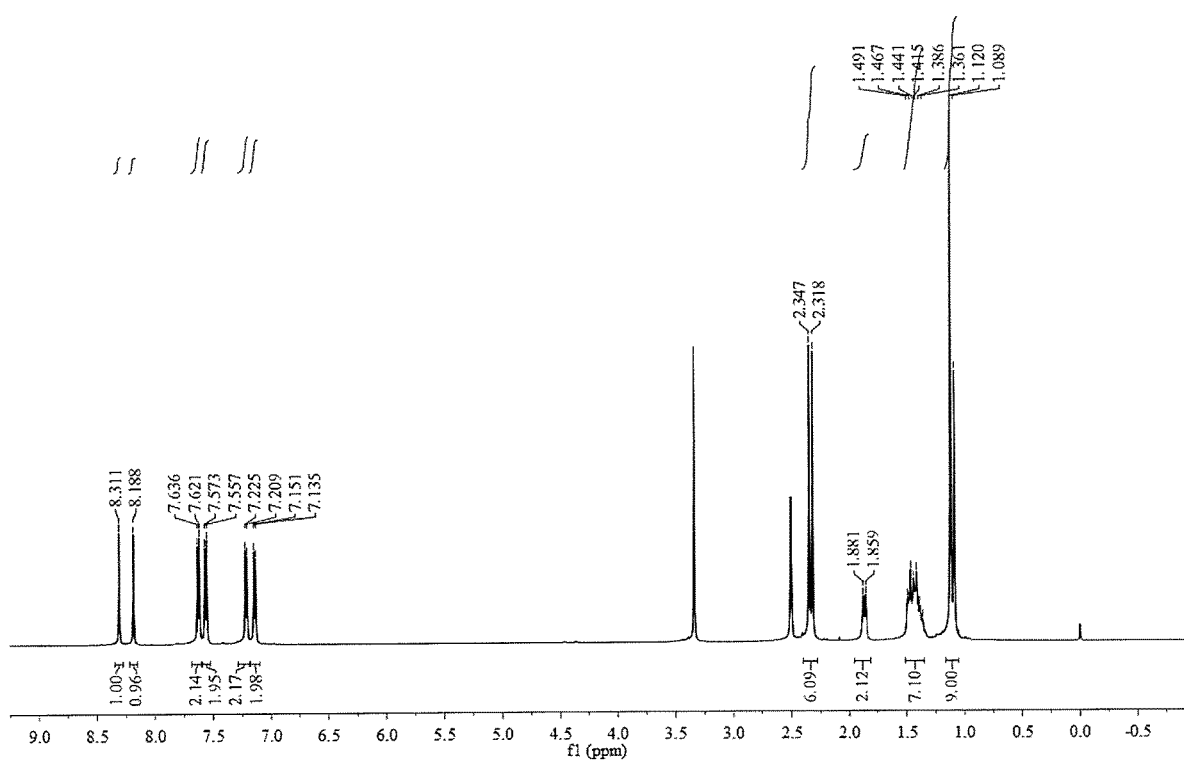
FIG. 3 is a $^1H$ NMR graph of 1,8-bis(4-methylphenylimine)-p-menthane.
Figure 4:
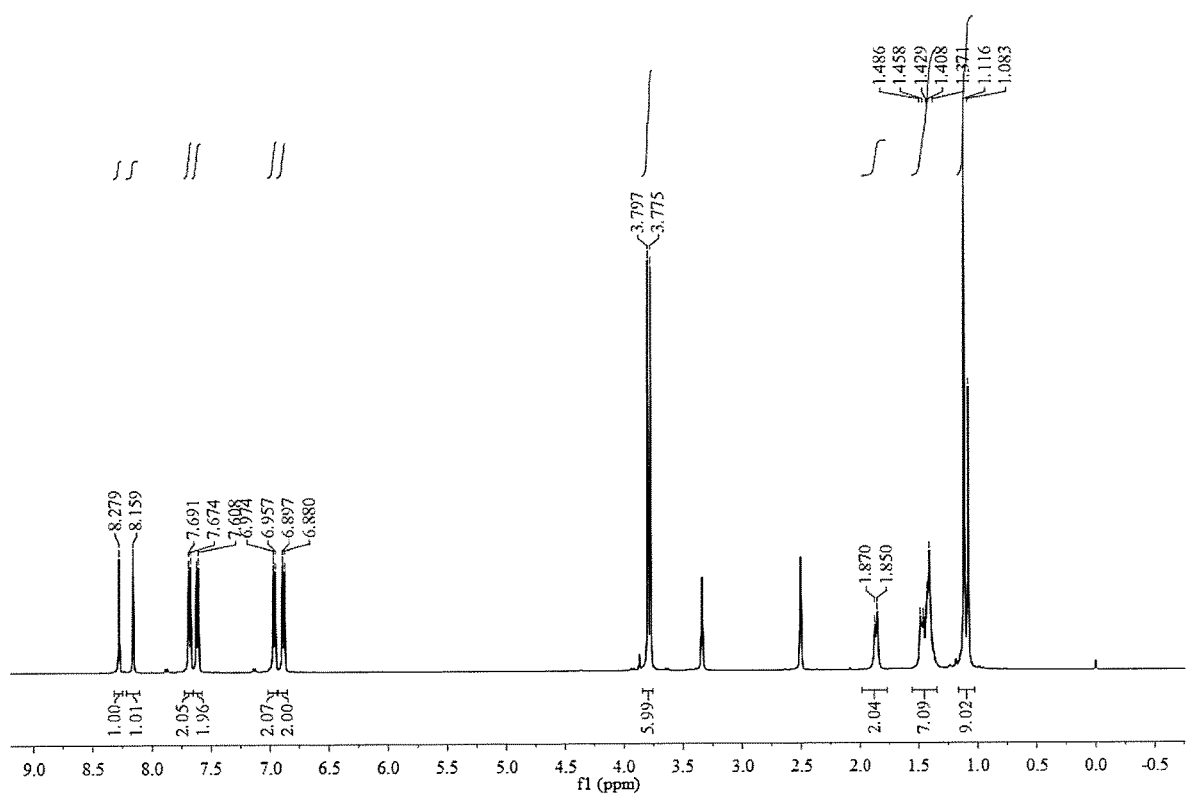
FIG. 4 is a $^1H$ NMR graph of 1,8-bis(4-methoxyphenylimine)-p-menthane.
Figure 5:
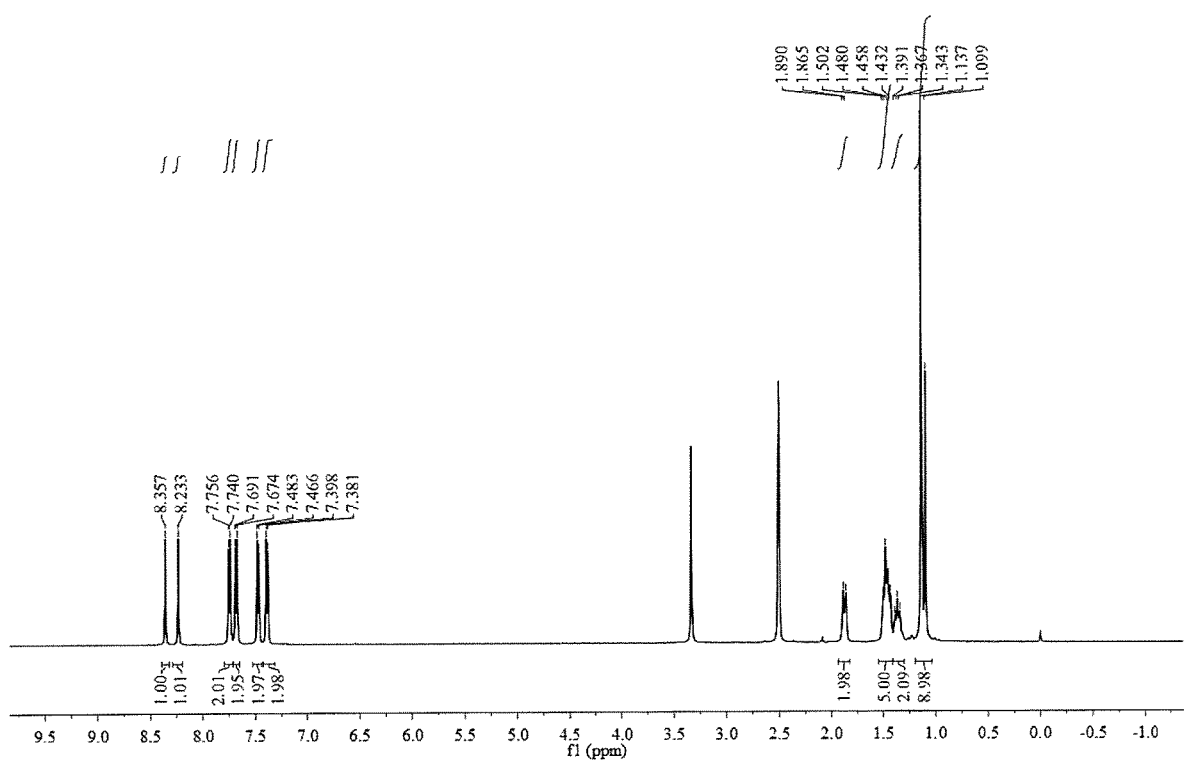
FIG. 5 is a $^1H$ NMR graph of 1,8-bis(4-chlorophenylimine)-p-menthane.
Figure 6:
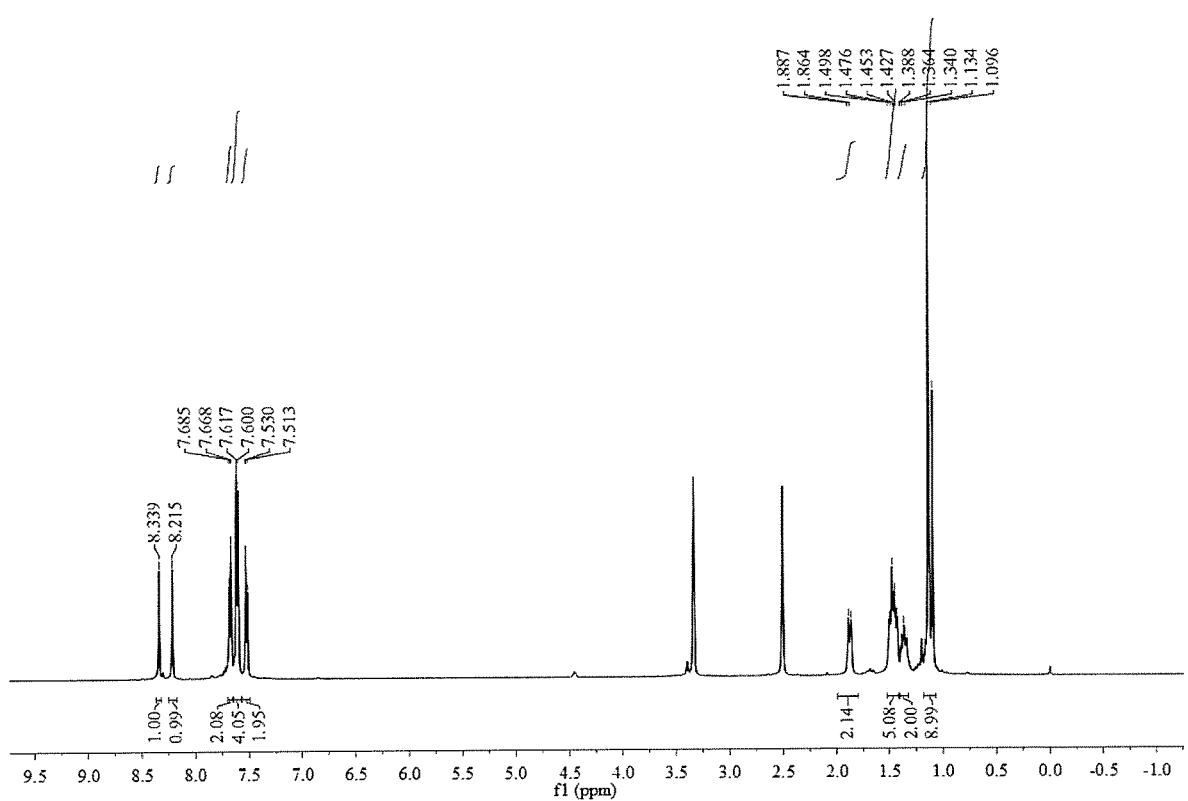
FIG. 6 is a $^1H$ NMR graph of 1,8-bis(4-bromophenylimine)-p-menthane.
Figure 7:
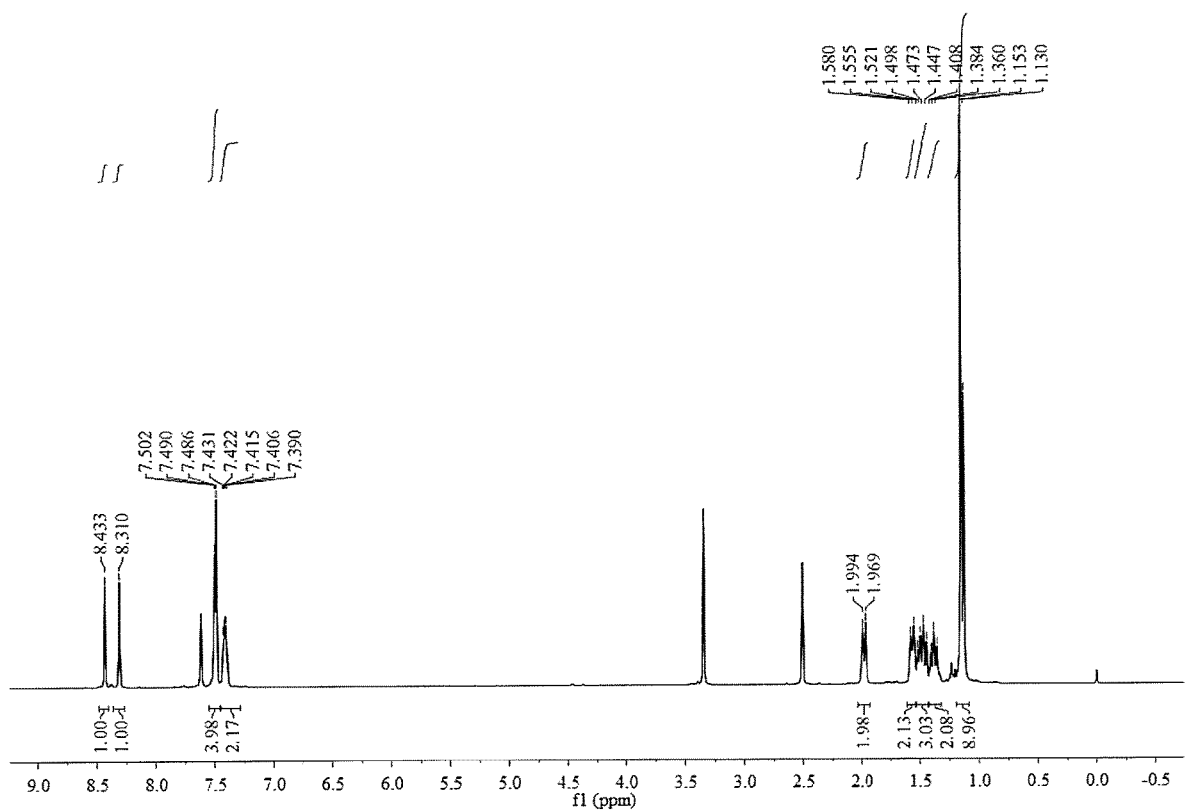
FIG. 7 is a $^1H$ NMR graph of 1,8-bis(2,6-dichlorophenylimine)-p-menthane.
Figure 8:
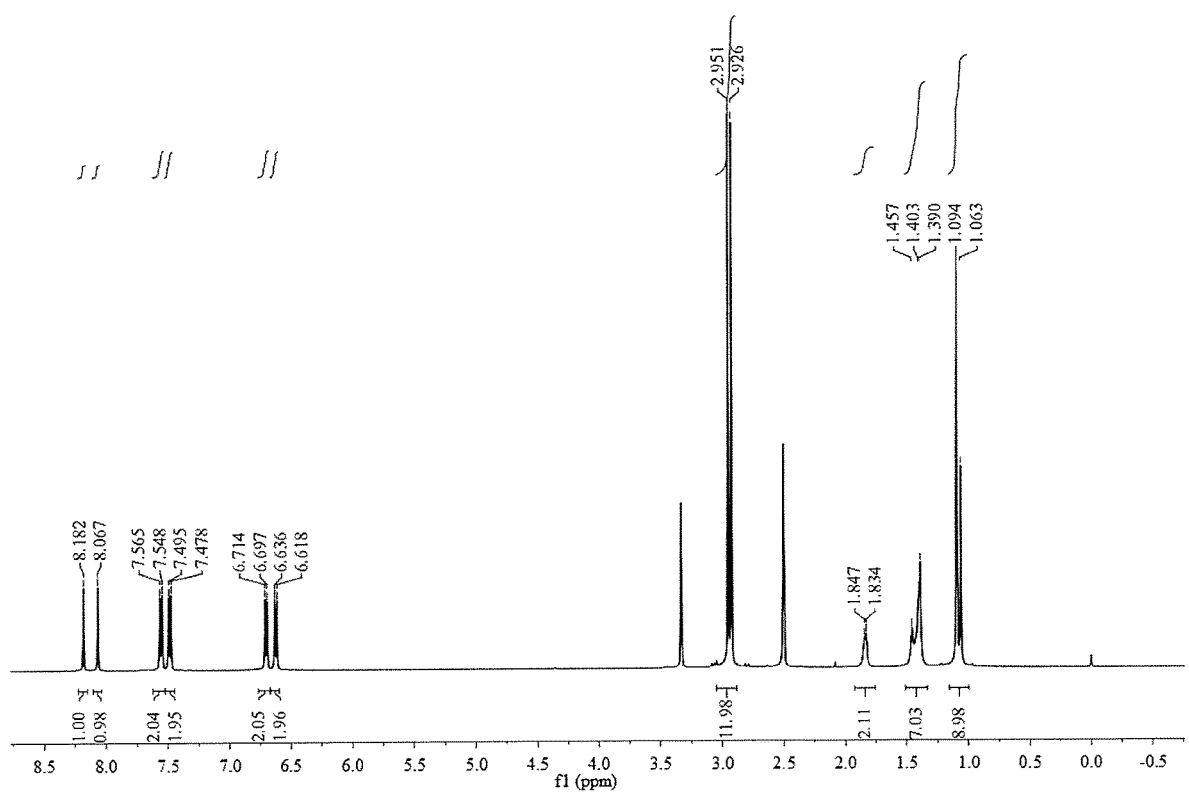
FIG. 8 is a $^1H$ NMR graph of 1,8-bis(p-dimethylaminophenylimine)-p-menthane.
Figure 9:
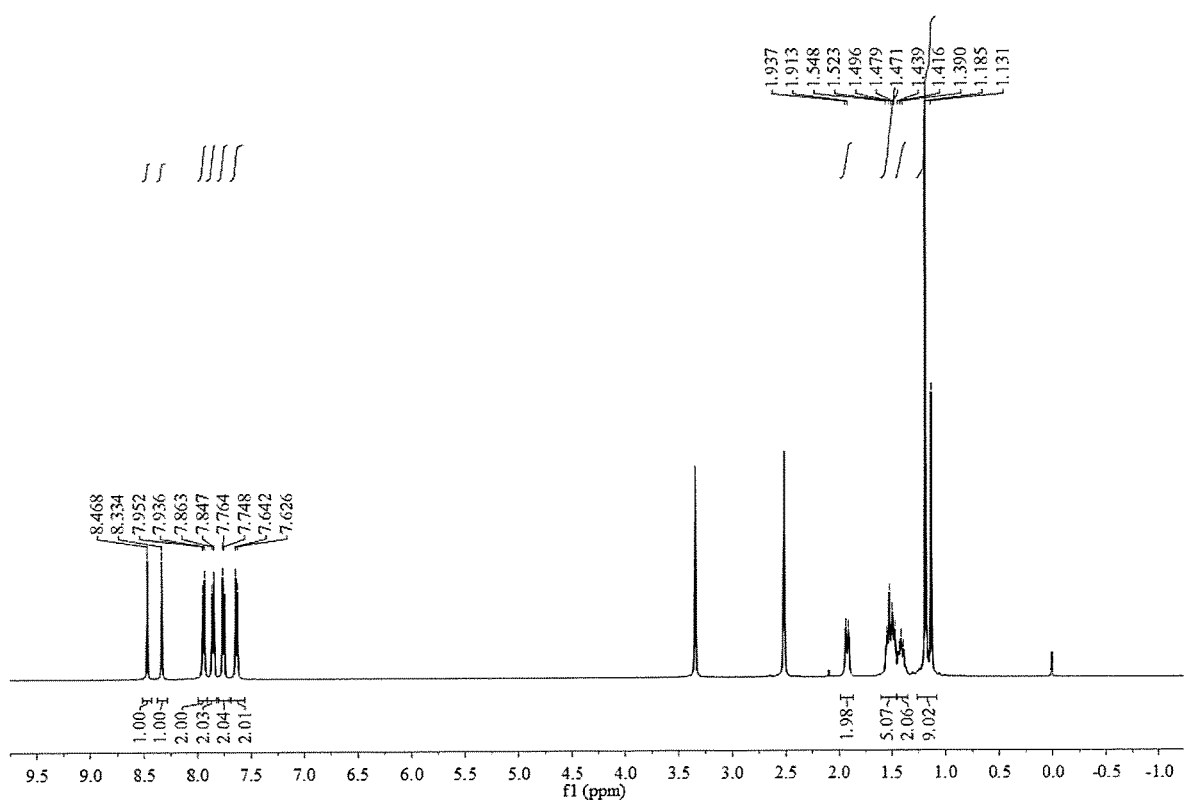
FIG. 9 is a $^1H$ NMR graph of 1,8-bis(p-trifluoromethylphenylimine)-p-menthane.
Figure 10:
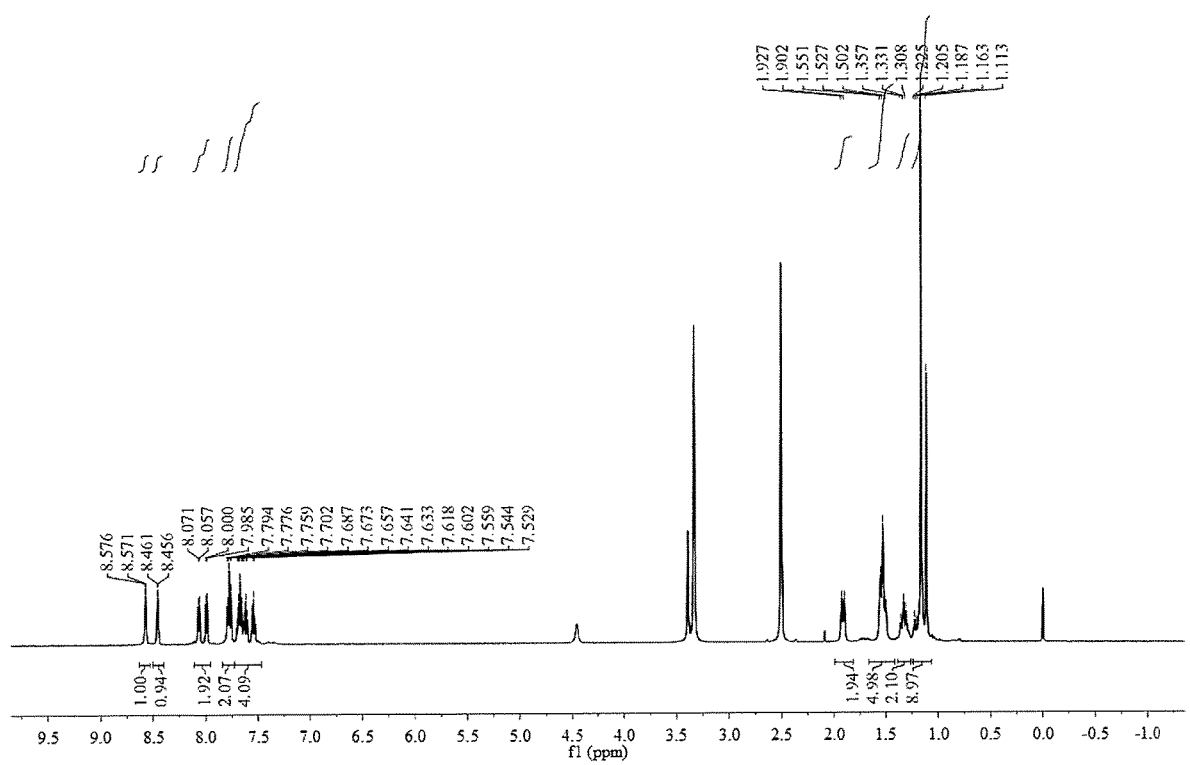
FIG. 10 is a $^1H$ NMR graph of 1,8-bis(2-trifluoromethylphenylimine)-p-menthane.
Figure 11:
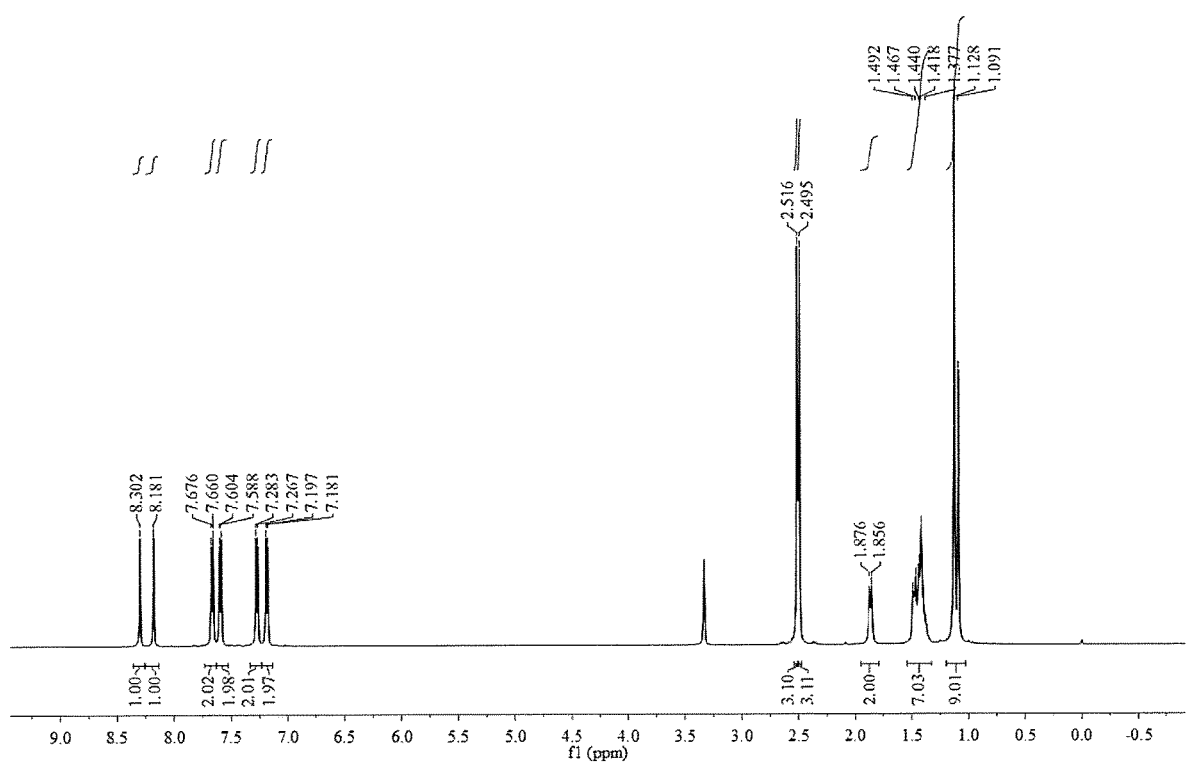
FIG. 11 is a $^1H$ NMR graph of 1,8-bis(p-methylthiophenylimine)-p-menthane.

The gas-phase peak area normalization method was used to analyze the products. Gas phase conditions: Shimadzu GC-2014AF; the carrier gas $N_2$ pressure was 0.6 MPa; the air pressure was 0.6 MPa, and the $H_2$ pressure was 0.6 MPa. The programmed heating method was used. The temperature rise program was as follows: 70° C. (kept for 2 min, rate 3° C./min)→130° C. (kept for 0 min, rate 10° C./min)→270° C. (kept for 2 min).

Preparation Method

A type of 1,8-bis(Schiff base)-p-menthane derivatives as well as their preparation method are disclosed in the invention. A 1,8-bis(Schiff base)-p-menthane derivative was prepared by using 1,8-diamino-p-menthane to be reacted with a substituted benzaldehyde in a polar organic solvent. After the completion of the reaction, the solvent was distilled to perform recrystallization to get the 1,8-bis(Schiff base)-p-menthane derivative product. Pre-emergence herbicidal activity against ryegrass was determined by using the Petri dish seed germination method. The 1,8-bis(Schiff base)-p-menthane derivative has the following structure:

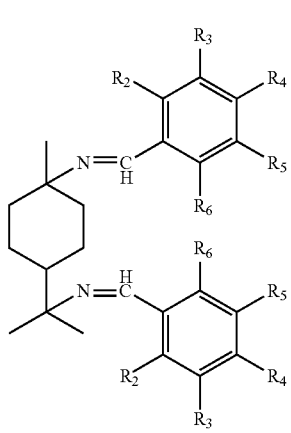

In the general formula I, $R_1$~$R_6$ are one or more of hydrogen, an alkyl group, a halogenated alkyl group, a nitro group, a halogen group, or any combinations thereof.

The above-mentioned polar organic solvent is any one of methanol, ethanol, tetrahydrofuran, dimethylformamide and dimethylsulfoxide.

The reaction temperature is 0° C.~75° C., and the reaction time is 1~48 h.

After the completion of the reaction, part of the solvent was distilled off and the resultant was recrystallized to get a 1,8-bis(Schiffbase)-p-menthane derivative.

More Specific Steps are as Follows:

Step 1: 0.68 g (4 mmol) of 1,8-diamino-p-menthane is added into a three-necked flask containing 10 mL polar organic solvent, and 9.6 mmol of a substituted benzaldehyde dissolved in 10 mL polar organic solvent is slowly added dropwise into the flask with magnetic stirring; the mixture is then slowly heated to a certain reaction temperature and reacts for a certain time at the temperature; after the end of the reaction, part of the solvent is distilled, and the resultant stays static to precipitate and crystallize; the resulting crystalline powder is then filtrated and washed to get a 1,8-bis(Schiffbase)-p-menthane derivative. Wherein, the polar organic solvent is methanol, ethanol, tetrahydrofuran, dimethylformamide or dimethylsulfoxide; the substituted groups of the substituted benzaldehyde are an alkyl group, a halogenated alkyl group, a nitro group, a halogen group, or any combinations thereof; the reaction temperature is 0° C.~75° C., and the reaction time is 1-48 h. After the completion of the reaction, part of the solvent is distilled off and the resultant is recrystallized to obtain the 1,8-bis(Schiff base)-p-menthane derivative product.

Step 2: accurately weigh 1 mmol of the 1,8-bis(Schiff base)-p-menthane derivative and dissolve it in 0.25 mL DMF, and then add a drop of Tween 80 into it; after the product is fully dissolved, the resulting solution is transferred to a 100 mL volumetric flask and is diluted with distilled water to the mark to obtain a solution having a concentration of 10 mmol/L as the mother liquor. Using the two-fold dilution method, a series of diluted sample solutions with different concentrations are prepared with the mother liquor (the concentrations of DMF and Tween 80 in the diluted solutions should be consistent with those in the mother liquor).

The annual ryegrass seeds are soaked with distilled water for 15 h. Place a piece of filter paper on the bottom of a Petri dish (φ9 cm), add 10 mL of the above sample solution having the corresponding concentration into it, respectively, and add the same amount of the mixture of water, DMF and Tween 80 into such a Petri dish as a blank control. Place 10 grains of seeds into each dish. The dishes are then placed in an incubator and cultured at 25° C. for 5 days. The experimental data are analyzed with DPS software, and the inhibition rate of the 1,8-bis(Schiff base)-p-menthane derivative on the root or stem growth of ryegrass seeds is calculated as follows:

$$y = \frac{x_2 - x_1}{x_2}$$

Where: y is the inhibition rate on the root or stem growth, $x_2$ is the root length or stem length of the control sample, and $x_1$ is the root length or stem length of the sample.

Example 1

0.68 g (4 mmol) of 1,8-diamino-p-menthane [homemade. For its preparation method, please refer to: ZL200610096308.6 (the implementation case in "A Method for Preparing 1,8-Diamino-p-menthane from 1,8-Terpene Diol" by Zhao Zhendong, Feng Zhiyong, Bi Liangwu, et al.) or ZL 201610455121.4 (the example in "A Method for Preparing 1,8-Diamino-p-menthane from Unsaturated Turpentine Monoterpene" by Xu Shichao, Zhao Zhendong, Zhu Shouji, et al.)] was added into a three-necked flask containing 10 mL ethanol, and 9.6 mmol of 2-hydroxybenzaldehyde dissolved in 10 mL polar organic solvent was slowly added dropwise into the flask with magnetic stirring; the mixture reacted for 12 h at the room temperature; after the end of the reaction, part of the solvent was distilled, and the resultant stayed static to precipitate and crystallize; the resulting crystalline powder was then filtrated and washed to get 1,8-bis(2-hydroxyphenylimine)-p-menthane. The yield was 90.7%.

1 mmol of the 1,8-bis(2-hydroxyphenylimine)-p-menthane was accurately weighed and dissolved in 0.25 mL DMF; a drop of Tween 80 was then added into it; after the product was fully dissolved, the resulting solution was transferred to a 100 mL volumetric flask and was diluted with distilled water to the mark to obtain a solution having a concentration of 10 mmol/L as the mother liquor. Using the two-fold dilution method, a series of diluted sample solutions with different concentrations (5 mmol/L, 2.5 mmol/L, 1.25 mmol/L, 0.625 mmol/L and 0.3125 mmol/L; the concentrations of DMF and Tween 80 in the diluted solutions should be consistent with those in the mother liquor) were prepared with the mother liquor.

The annual ryegrass seeds were soaked with distilled water for 15 h. Placed a piece of filter paper on the bottom of a Petri dish (φ 9 cm), added 10 mL of the above sample solution having the corresponding concentration into it, respectively, and added the same amount of the mixture of water, DMF and Tween 80 into such a Petri dish as a blank control. 10 grains of seeds were placed into each of the dishes. The dishes were then placed in an incubator and cultured at 25° C. for 5 days. The experimental data were analyzed with DPS software, and the inhibition rates of 10 mmol/L, 5 mmol/L, 2.5 mmol/L, 1.25 mmol/L, 0.625 mmol/L and 0.3125 mmol/L 1,8-bis(2-hydroxyphenylimine)-p-menthane solutions on the root growth of ryegrass seeds were 100.0%, 100.0%, 83.3%, 62.2%, 41.4% and 14.3%, respectively; and their inhibition rates on the stem growth of ryegrass seeds were 100.0%, 100.0%, 79.5%, 61.7%, 38.0% and 6.9%, respectively.

Example 2

Except that the added substituted benzaldehyde was p-fluorobenzaldehyde and the reaction time was 8 h, other operation procedures are the same as those of Example 1. The yield of the target product 1,8-bis(4-fluorophenylimine)-p-menthane was 53.7%. The inhibition rates of 10 mmol/L, 5 mmol/L, 2.5 mmol/L, 1.25 mmol/L, 0.625 mmol/L and 0.3125 mmol/L 1,8-bis(4-fluorophenylimine)-p-menthane solutions on the root growth of ryegrass seeds were: 94.9%, 85.5%, 78.0%, 58.0%, 35.0% and 14.0%, respectively; and their inhibition rates on the stem growth of ryegrass seeds were: 94.9%, 82.5%, 53.8%, 49.9%, 21.6%, 4.5%, respectively.

Example 3

Except that the added substituted benzaldehyde was p-methylbenzaldehyde and the reaction time was 15 h, other operation procedures are the same as those of Example 1. The yield of the target product 1,8-bis(4-methylphenylimine)-p-menthane was 56.1%. The inhibition rates of 10 mmol/L, 5 mmol/L, 2.5 mmol/L, 1.25 mmol/L, 0.625 mmol/L and 0.3125 mmol/L 1,8-bis(4-methylphenylimine)-p-menthane solutions on the root growth of ryegrass seeds were: 100.0%, 92.8%, 67.0%, 34.2%, 26.3% and 20.3%, respectively; and their inhibition rates on the stem growth of ryegrass seeds were: 100.0%, 90.4%, 46.2%, 26.8%, 25.9% and 11.1%, respectively.

Example 4

Except that the added substituted benzaldehyde was p-methoxybenzaldehyde and the reaction time was 18 h, other operation procedures are the same as those of Example 1. The yield of the target product 1,8-bis(4-methoxyphenylimine)-p-menthane was 48.0%. The inhibition rates of 10 mmol/L, 5 mmol/L, 2.5 mmol/L, 1.25 mmol/L, 0.625 mmol/L and 0.3125 mmol/L 1,8-bis(4-methoxyphenylimine)-p-menthane solutions on the root growth of ryegrass seeds were: 100.0%, 100.0%, 88.3%, 54.3%, 15.5% and 12.5%, respectively; and their inhibition rates on the stem growth of ryegrass seeds were: 100.0%, 100.0%, 73.9%, 48.2%, 32.2% and 30.6%, respectively.

Example 5

Except that the added substituted benzaldehyde was p-chlorobenzaldehyde and the reaction time was 8 h, other operation procedures are the same as those of Example 1. The yield of the target product 1,8-bis(4-chlorophenylimine)-p-menthane was 56.7%. The inhibition rates of 10 mmol/L, 5 mmol/L, 2.5 mmol/L, 1.25 mmol/L, 0.625 mmol/L and 0.3125 mmol/L 1,8-bis(4-chlorophenylimine)-p-menthane solutions on the root growth of ryegrass seeds were: 100.0%, 100.0%, 100.0%, 99.3%, 98.0% and 94.1%, respectively; and their inhibition rates on the stem growth of ryegrass seeds were: 100.0%, 100.0%, 98.2%, 91.4%, 90.3% and 75.2%, respectively.

Example 6

Except that the added substituted benzaldehyde was p-bromobenzaldehyde and the reaction time was 8 h, other operation procedures are the same as those of Example 1. The yield of the target product 1,8-bis(4-bromophenylimine)-p-menthane was 73.7%. The inhibition rates of 10 mmol/L, 5 mmol/L, 2.5 mmol/L, 1.25 mmol/L, 0.625 mmol/L and 0.3125 mmol/L 1,8-bis(4-bromophenylimine)-p-menthane solutions on the root growth of ryegrass seeds were: 100.0%, 100.0%, 100.0%, 100.0%, 88.0% and 71.0%, respectively; and their inhibition rates on the stem growth of ryegrass seeds were: 100.0%, 100.0%, 100.0%, 100.0%, 79.5% and 64.8%, respectively.

Example 7

Except that the added substituted benzaldehyde was 2,6-dichlorobenzaldehyde and the reaction time was 6 h, other operation procedures are the same as those of Example 1. The yield of the target product 1,8-bis(2,6-dichlorophenylimine)-p-menthane was 62.8%. The inhibition rates of 10 mmol/L, 5 mmol/L, 2.5 mmol/L, 1.25 mmol/L, 0.625 mmol/L and 0.3125 mmol/L 1,8-bis(2,6-dichlorophenylimine)-p-menthane solutions on the root growth of ryegrass seeds were: 100.0%, 100.0%, 100.0%, 100.0%, 100.0% and 100.0%, respectively; and their inhibition rates on the stem growth of ryegrass seeds were: 100.0%, 100.0%, 100.0%, 100.0%, 100.0% and 100.0%, respectively.

Example 8

Except that the added substituted benzaldehyde was p-dimethylaminobenzaldehyde and the reaction time was 18 h, other operation procedures are the same as those of Example 1. The yield of the target product 1,8-bis(p-dimethylaminophenylimine)-p-menthane was 60.0%. The inhibition rates of 10 mmol/L, 5 mmol/L, 2.5 mmol/L, 1.25 mmol/L, 0.625 mmol/L and 0.3125 mmol/L 1,8-bis(p-dimethylaminophenylimine)-p-menthane solutions on the root growth of ryegrass seeds were: 100.0%, 100.0%, 100.0%, 100.0%, 100.0% and 100.0%, respectively; and their inhibition rates on the stem growth of ryegrass seeds were: 100.0%, 100.0%, 100.0%, 100.0%, 100.0% and 96.8%, respectively.

Example 9

Except that the added substituted benzaldehyde was p-trifluoromethylbenzaldehyde and the reaction time was 10 h, other operation procedures are the same as those of Example 1. The yield of the target product 1,8-bis(p-trifluoromethylphenylimine)-p-menthane was 44.5%. The inhibition rates of 10 mmol/L, 5 mmol/L, 2.5 mmol/L, 1.25 mmol/L, 0.625 mmol/L and 0.3125 mmol/L 1,8-bis(p-trifluoromethylphenylimine)-p-menthane solutions on the root growth of ryegrass seeds were: 93.8%, 81.7%, 87.5%, 65.8%, 45.5% and 35.4%, respectively; and their inhibition rates on the stem growth of ryegrass seeds were: 87.9%, 34.8%, 53.7%, 26.0%, 2.4% and 1.1%, respectively.

Example 10

Except that the added substituted benzaldehyde was 2-trifluoromethylbenzaldehyde and the reaction time was 10 h, other operation procedures are the same as those of Example 1. The yield of the target product 1,8-bis(2-trifluoromethylphenylimine)-p-menthane was 51.3%. The inhibition rates of 10 mmol/L, 5 mmol/L, 2.5 mmol/L, 1.25 mmol/L, 0.625 mmol/L and 0.3125 mmol/L 1,8-bis(2-trifluoromethylphenylimine)-p-menthane solutions on the root growth of ryegrass seeds were: 100.0%, 100.0%, 100.0%, 99.7%, 86.2% and 79.2%, respectively; and their inhibition rates on the stem growth of ryegrass seeds were: 100.0%, 100.0%, 100.0%, 88.2%, 56.3% and 56.3%, respectively.

Example 11

Except that the added substituted benzaldehyde was p-methylthiobenzaldehyde and the reaction time was 12 h, other operation procedures are the same as those of Example 1. The yield of the target product 1,8-bis(p-methylthiophenylimine)-p-menthane was 46.2%. The inhibition rates of 10 mmol/L, 5 mmol/L, 2.5 mmol/L, 1.25 mmol/L, 0.625 mmol/L and 0.3125 mmol/L 1,8-bis(p-methylthiophenylimine)-p-menthane solutions on the root growth of ryegrass seeds were: 67.8%, 50.3%, 54.8%, 35.4%, 46.4% and 37.7%, respectively; and their inhibition rates on the stem growth of ryegrass seeds were: 36.7%, 21.9%, 28.0%, 27.1%, 28.7% and 20.8%, respectively.

Example 12

Except that the reaction time was 1 h, other operation procedures are the same as those of Example 1. The yield of the target product 1,8-bis(2-hydroxyphenylimine)-p-menthane was 17.7%, respectively.

Example 13

Except that the reaction time was 48 h, other operation procedures are the same as those of Example 1. The yield of the target product 1,8-bis(2-hydroxyphenylimine)-p-menthane was 88.2%, respectively.

Example 14

Except that the reaction temperature was 0° C., other operation procedures are the same as those of Example 1. The yield of the target product 1,8-bis(2-hydroxyphenylimine)-p-menthane was 28.8%, respectively.

Example 15

Except that the reaction temperature was 75° C., other operation procedures are the same as those of Example 1. The yield of the target product 1,8-bis(2-hydroxyphenylimine)-p-menthane was 94.1%, respectively.

Example 16

Except that the reaction solvent was methanol, other operation procedures are the same as those of Example 1. The yield of the target product 1,8-bis(2-hydroxyphenylimine)-p-menthane was 89.3%, respectively.

Example 17

Except that the reaction solvent was dimethyl sulfoxide, other operation procedures are the same as those of Example 1. The yield of the target product 1,8-bis(2-hydroxyphenylimine)-p-menthane was 19.7%, respectively.

What is claimed is:

1. A 1,8-bis(Schiff base)-p-menthane derivative, wherein the derivative has the chemical structure of formula I,

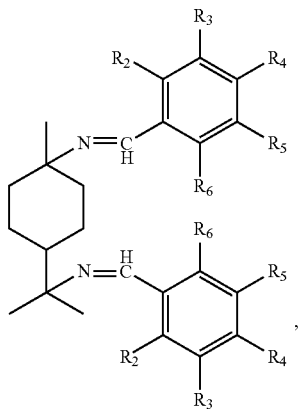

wherein
$R_2$, $R_3$, $R_4$, $R_5$, and $R_6$ are defined such that the derivative is any one of the following compounds:
1,8-bis(2-hydroxyphenylimine)-p-menthane,
1,8-bis(4-fluorophenylimine)-p-menthane,
1,8-bis(4-methylphenylimine)-p-menthane,
1,8-bis(4-methoxyphenylimine)-p-menthane,
1,8-bis(4-chlorophenylimine)-p-menthane,
1,8-bis(4-bromophenylimine)-p-menthane,
1,8-bis(2,6-dichlorophenylimine)-p-menthane,
1,8-bis(p-dimethylaminophenylimine)-p-menthane,
1,8-bis(p-trifluoromethylphenylimine)-p-menthane,
1,8-bis(2-trifluoromethylphenylimine)-p-menthane, or
1,8-bis(p-methylthiophenylimine)-p-menthane.

2. A preparation method of the compound of claim 1, comprising:
reacting 1,8-diamino-p-menthane with a substituted benzaldehyde in a polar organic solvent to obtain the derivative of claim 1; and
distilling the polar organic solvent to recrystallize the compound of claim 1.

3. The preparation method of claim 2, wherein the polar organic solvent is methanol, ethanol, tetrahydrofuran, dimethylformamide, or dimethylsulfoxide.

4. The preparation method of claim 2, wherein a substituent of the substituted benzaldehyde is a hydroxyl group, an alkyl group, a halogenated alkyl group, a nitro group, a halogen group, or any combinations thereof.

5. The preparation method of claim 2, wherein a reaction temperature of the reacting step is 0-75° C.

6. The preparation method of claim 2, wherein a reaction time of the reacting step is 1-48 hours.

7. A herbicide, wherein an active ingredient of the herbicide comprises the compound of claim 1.

8. A herbicide of ryegrass, wherein an active ingredient of the herbicide comprises the compound of claim 1.

* * * * *